United States Patent [19]

Taylor

[11] Patent Number: 5,373,160
[45] Date of Patent: Dec. 13, 1994

[54] REMOTE HAZARDOUS AIR PULLUTANTS MONITOR

[75] Inventor: Lyle H. Taylor, Murrysville, Pa.

[73] Assignee: Westinghouse Electric Corporation, Pittsburgh, Pa.

[21] Appl. No.: 58,191

[22] Filed: May 4, 1993

[51] Int. Cl.$^5$ .................. G01N 21/17; G01N 21/35
[52] U.S. Cl. ................ 250/338.5; 250/339.01; 250/339.12; 250/340; 250/347; 250/349
[58] Field of Search ............ 250/338.5, 339, 340, 250/341, 343, 347, 339.01, 339.07, 339.12, 349; 356/437, 438

[56] References Cited

U.S. PATENT DOCUMENTS

| | | | |
|---|---|---|---|
| 3,805,196 | 4/1974 | Feichtner et al. | 333/30 R |
| 3,829,694 | 8/1974 | Goto | 250/338.5 |
| 4,450,356 | 5/1984 | Murray et al. | 250/338.5 X |
| 4,490,845 | 12/1984 | Steinbruegge et al. | 382/1 |
| 4,496,839 | 1/1985 | Bernstein et al. | 250/341 |
| 4,505,550 | 3/1985 | Steinbruegge | 350/372 |
| 4,575,186 | 3/1986 | Gottlieb et al. | 350/358 |
| 4,622,845 | 11/1986 | Ryan et al. | 73/24 |
| 4,652,756 | 3/1987 | Ryan et al. | 250/343 |
| 4,663,961 | 5/1987 | Nelson et al. | 73/24 |
| 4,676,642 | 6/1987 | French | 356/346 |
| 4,705,362 | 11/1987 | Ryan et al. | 350/372 |
| 4,810,884 | 3/1989 | Carlson | 250/338.5 |
| 4,937,447 | 6/1990 | Barrett | 250/338.5 X |
| 5,120,961 | 6/1992 | Levin et al. | 250/343 X |
| 5,216,484 | 6/1993 | Chao et al. | 250/339 X |
| 5,294,796 | 3/1994 | Fee | 250/338.5 |

OTHER PUBLICATIONS

Marten et al., "An Advantageous Technique of Stratospheric Emission Spectrometry in the Far Infrared", Infrared Physics, vol. 15, No. 3, Sep. 1975, pp. 205–209.
Murray et al., "Remote Measurement of HCl, CH$_4$, and N$_2$O Using a Single-Ended Chemical-Laser Lidar System," Applied Optics, vol. 15, No. 12, Dec. 1976, pp. 3140–3148.
Efficient Second Harmonic Generation in Tl$_3$AsSe$_3$ Using Focussed CO$_2$ Laser Radiation, D. R. Suhre, Appl. Phys. 1991, B52:367–70.

*Primary Examiner*—Constantine Hannaher
*Assistant Examiner*—Edward J. Glick

[57] ABSTRACT

Gases such as pollutants are discerned in the open air, preferably using a laser to emit an infrared light beam along a sight path for illuminating the gases. A telescope is directed along the sight path and collects light from the gases, the combination of the laser and telescope permitting redirection of the sight path to any target, such as fugitive emissions of a stack. An optical tunable filter is coupled to the telescope for selecting a particular optical wavelength or band, and focusing the filtered wavelength on a detector. A processor 72) is coupled to the detector output and pulses the laser. The processor analyzes the light levels as a function of wavelength to discriminate for the presence of selected gases by determining a characteristic pattern of light absorption and light emission by the gases. The tunable filter has an acousto-optical crystal of Tl$_3$AsSe$_3$, in which an RF acoustic wave is generated for varying diffraction of light by the filter, thereby selecting a wavelength. A nonlinear output crystal selectively generates harmonics for increasing wavelength coverage, and can also be Tl$_3$AsSe$_3$. When the laser is off, the filter acts on infrared emissions of the gases. Sensitivity to narrow emission lines is increased by modulating the RF drive to the tunable filter, producing derivatives of the spectra.

19 Claims, 1 Drawing Sheet

REMOTE HAZARDOUS AIR PULLUTANTS MONITOR

BACKGROUND OF THE INVENTION

1. Field of the Invention

The invention relates to methods and apparatus for monitoring air quality, in particular for identification of airborne molecules, concentration measurements, and measurement of the dimensions of localized concentrations, for example the emissions of a particular stack of a manufacturing plant. A combination of long path infrared absorption and emission spectroscopy, and range finding, is effected by an automatically controlled and redirectable spectroscopic device.

A pulsed $CO_2$ laser is aligned with a receiving telescope and can be directed selectively through or around a doubler crystal for operation in different frequency bands. An electro-acoustic tunable filter and detector arrangement discriminates for absorption and emission at particular frequencies characteristic of pollutant gases, and a computer decodes the timing and absorption/emission information as a function of optical wavelength and distance. The computer preferably also generates and records a profile of gas concentrations along the redirectable sight path, including the concentrations of hazardous pollutant gases.

2. Prior Art

Infrared spectroscopy is a known method for assessing concentrations of gases in samples. Systems that use a laser and an acousto-optic tunable filter are disclosed, for example, in U.S. Pat. Nos. 4,490,845—Steinbruegge et al; 4,622,845—Ryan et al; and 4,652,756—Ryan et al. The technique generally involves passing an infrared band laser beam from a source to a detector, across the flowpath of gases in a stack. Reflectors can be used to pass the beam across the stack more than once, thus increasing the extent to which the beam is affected by the sample of gases in the stack. Typically, however, the path of the beam is "closed," i.e., the light passes from the source, through the gas, to the detector. Gases in the stack absorb the illuminating radiation selectively at specific frequencies due to the molecular and atomic structure of the gas molecules. The detector discriminates for known patterns of absorption, i.e., absorption at certain wavelengths and not at other wavelengths.

Gas also may emit radiation at specific frequencies due to fluorescence effects following the application of sufficient excitation energy or by thermal excitation which produces blackbody radiation. Fluorescence effects are a form of reflectance. Normally, fluorescence is very low in power compared to the illuminating energy. Thus fluorescence is difficult to detect in a closed path arrangement during illumination, or in a closed path arrangement wherein the detector determines absorption as a function of wavelength in the range of illumination. Fluorescence measurements also typically are conducted at close range, to enable application of sufficient excitation energy to produce a detectable response. By analyzing the energy received as a function of frequency or wavelength, it is possible to detect the presence of particular molecules, and to assess the concentration of these molecules in the stack gases. According to the patents to Ryan et al, stack monitoring is done repetitively in an automated manner using a computer controller and analyzer for controlling a tunable filter at the receiver.

Monitoring stack gases requires a detection arrangement that is fixed and applicable only to measure the instantaneous concentration(s) of gas(es) in the stack. In conjunction with a flow measurement technique, this information can be converted into a gas volume figure that may be meaningful with respect to any air pollution at large. However, it would be advantageous to enable fast and automated measurements in the open air, and to provide a system with the versatility needed to discriminate for a wide variety of gases.

In general, there are five open path remote sensing techniques applicable to assessment of gas concentrations in the air. These are fluorescence, differential optical absorption spectroscopy, tunable diode laser absorption spectroscopy, differential absorption lidar spectroscopy, and Fourier transform infrared spectroscopy. These are each methods for measuring the wavelength-specific behavior of the gas molecules such that characteristic patterns that represent particular gases can be identified in the data.

The fluorescence technique measures the light intensity emitted by specific gases at characteristic wavelengths. The light is emitted when electrons in the gas molecules return to a lower energy state after the molecules have been excited, typically by radiation from a high intensity light source. Fluorescence measurement is restricted to measurements in the ultraviolet, where OH radicals and $SO_2$ can be effectively discriminated by characteristic spectroscopic signatures. However, expensive equipment is required and the equipment is designed to measure only for specific pollutants. The technique lacks versatility and is operable only with respect to a sample that is very close to the illumination source and the detector.

Differential optical absorption spectroscopy involves measuring the differential intensities between absorption peaks and valleys versus wavelength in the ultraviolet-to-visible regions. The light source is usually a high intensity lamp and the maximum path length is around 800 m. This method has good specificity for discriminating among gases, and is the only method that effectively measures $NO_3$ radicals. Equipment for making the measurements is readily available, for example as embodied in the OPSIS system, installed at various locations in Europe. However, because the system does not encompass the mid-to-far infrared spectral band, it is ineffective for discriminating most molecular hydrocarbon concentrations, which unfortunately include many pollutants that it would be desirable to detect.

Mid-IR tunable diode lasers are available for tunable diode laser absorption spectroscopy. A tunable light source, as opposed to a wide band light source, can simplify the equipment required for light absorption spectroscopy because the sample can be illuminated at the wavelengths of interest, and the absorption of the light at these frequencies can be examined. The tunable diode approach has high time resolution, excellent specificity, high sensitivity for $NO_2$, and also measures $HNO_3$, $NH_3$, $HCHO$ and $H_2O_2$ at trace levels. It detects pollutants that other techniques cannot, and/or has a higher sensitivity due to precise control of illumination wavelength. However, laser diodes of sufficient power do not exist for the far-IR region where most hydrocarbon pollutants absorb. In the wavelengths where tunable diode lasers operate, power constraints of the source and sensitivity limitations of detectors limit atmospheric absorption measurements to a path length of about 300 m.

Instead of using fixed reflection targets, differential absorption lidar spectroscopy uses atmospheric backscatter of tunable pulsed lasers. This technique measures absorption and has been most successful in the ultraviolet and visible regions, where molecular scattering is prevalent. In the IR band, aerosols must provide the scattering. This technique has the advantage that range-resolved profiles over a substantial distance (e.g., 3 km) can be developed, i.e., the concentrations of detected gases as a function of distance from the source/detector. The present invention also uses a pulsed laser and has a ranging capability, which enables localization and volume measurements of pollution clouds. The invention, however, is arranged to operate in the mid-to-far infrared, and uses a tunable receiver.

Fourier transform infrared spectroscopy involves interferometry. A beam from a high intensity lamp is propagated through the atmosphere and split into two beams at the receiver. One beam is directed to a fixed mirror and the other beam to a moving mirror. The two beams are recombined to form an interferogram from which the absorption spectra is obtained. This technique is useful in the two IR atmospheric transmission windows where many toxic pollutant chemicals absorb, i.e., 3.3 to 4.2 $\mu$m and 8.3 to 13.3 $\mu$m. The method is good for relatively high pollutant concentrations, but it is limited in that the sensitivity for most pollutants is not sufficient for ambient monitoring in moderately polluted or unpolluted areas, where it may be desirable to detect and measure for traces. Moreover, the range is limited to about 500 m.

Unless one desires to measure only for the specific type of gas and concentration range, and perhaps at a specific location for which the foregoing monitoring systems are respectively designed, more than one of them is needed to avoid the drawbacks of power, frequency and sensitivity limitations of each. It would be possible to combine all the foregoing types of monitors in one system, to provide a measurement and detection system that enjoyed the advantages of the respective techniques. This would be prohibitively expensive and complex.

According to the present invention, laser infrared spectroscopy techniques are applied to a redirectable sighting device having an automated tunable filter detector arrangement and a multi-band source having means for selectively directing an illuminating beam through a nonlinear crystal to produce harmonics. The tunable filter is preferably an acousto-optical tunable diffractor, e.g., comprising at least one crystal of thallium arsenic selenide ($Tl_3AsSe_3$) or any other acousto-optic material. This crystal has piezoelectric aspects, and is operable as a tunable diffractor by varying the frequency of a modulating electro-acoustic wave passed through the crystal by application of a radio frequency modulating field.

U.S. Pat. No. 3,805,196—Feichtner et al discloses how to make and use a thallium arsenic selenide or "TAS" crystal as a controllable diffractor. The acoustic wave generated in the crystal produces alternating compression and rarefaction fronts, which have different indices of refraction. The wave fronts form a diffraction grating that spreads the spectrum of light passed therethrough, and diverts the received beam as a function of wavelength. The angle of refraction of the grating can be increased with the frequency of the acoustic wave, and the amount of light diffracted increases with the intensity of the acoustic wave. Therefore, by varying the acoustic frequency the crystal is tuned such that a particular wavelength can be directed on a detector. Furthermore, the angular shift of the diffracted beam can be mostly compensated by creating a wedge at either the input or output optical face of the acousto-optic tunable filter, with the result that the diffracted beam always appears at the same angle to the detector irrespective of the acoustic frequency. The output of the detector is digitized and stored to develop absorption information as a function of optical wavelength. A computer then determines the concentrations of gases along the sight path from their characteristic absorption spectra.

U.S. Pat. No. 4,505,550—Steinbruegge discloses an acousto-optic tunable filter in infrared bandwidths, useful for imaging equipment. U.S. Pat. Nos. 4,575,186—Gottlieb et al, and 4,705,362—Ryan et al disclose variations including, for example, a plurality of crystal arrangements for operating in different bands to enlarge the bandwidth of the filter as a whole. Each of the foregoing patents is hereby incorporated as if set forth in full.

SUMMARY OF THE INVENTION

It is an object of the invention to provide a long path infrared spectrometer arrangement that is highly specific, versatile and inexpensive.

It is also an object of the invention to provide an automated spectrographic analyzer that can be redirected to test for fugitive emissions of specific target sites, measuring gases rapidly, in situ, and avoiding the loss of radicals.

It is a further object of the invention to employ acousto-optical crystals for controllable selection of illumination at basic and harmonic illumination wavelengths, and to selectively filter light reflections, absorptions and emissions of gases to identify particular molecules by detecting spectral patterns characteristic of the molecules.

It is another object of the invention to probe regions that are not accessible to point monitors, and to automatically control illumination and measurements for completing a scan for hazardous pollutants in a short time.

These and other objects are accomplished by selectively discerning gases such as pollutants in the open air, using a laser to emit an infrared light beam along a sight path through the air, thereby illuminating gases along the sight path. A telescope is directed along the same sight path, and collects light from the gases in the air, the combination of the laser and telescope permitting redirection of the sight path to any target, such as fugitive emissions of a stack. An optical tunable filter is coupled to the telescope for selecting a particular optical wavelength or band, and focusing the filtered wavelength on a detector. A processor is coupled to the detector output and also controls the laser. The processor analyzes the light levels as a function of wavelength to discriminate for the presence of selected gases by determining a characteristic pattern of light absorption and light emission by the gases. The tunable filter has a piezoelectric transducer crystal bonded to $Tl_3AsSe_3$ or another acousto-optical material. An alternating electric field is applied to a transducer bonded to the crystal to set up an acoustic wave for varying the wavelength of the light which is diffracted through the filter, thus selecting a wavelength. The electric field can be changed rapidly in frequency, to advance the detector arrangement from one wavelength to another, and collecting spectrographic information. A second crystal preferably is selectable by the controller, to generate harmonics as an alternate source of laser illumination in a different optical band. The second crystal, namely the output crystal, can also be $Tl_3AsSe_3$ or another nonlinear optical material. The output crystal is disposed between the laser and the sight path, and produces at least one harmonic wavelength, whereby the laser is selectively operable to illuminate the gases along the sight path at a plurality of illumination frequencies.

BRIEF DESCRIPTION OF THE DRAWINGS

The invention is illustrated with respect to particular embodiments that are exemplary rather than limiting. Reference should be made to the appended claims rather than the specific embodiments disclosed as examples, to assess the scope of the invention in which exclusive rights are claimed. In the drawings.

DETAILED DESCRIPTION OF THE PREFERRED EMBODIMENTS

The invention applies acousto-optic tunable filter technology and tunable laser capability in the mid to far infrared (IR) band, to provide an instrument for optical remote measurement of concentrations of atmospheric gases. A multitude of the hazardous air pollutants, including pollutants specified in the 1990 Clean Air Act Amendments can be distinguished in this manner, and furthermore, localized concentrations can be measured as to size, concentration and component molecules. In the mid to far IR, most hydrocarbons can be identified by their absorption spectra, thereby complementing measurements in ultraviolet (UV) and visible bands, where homonuclear and light molecules have their main absorption spectra.

The measurement according to the invention is very fast. For example, 2 minutes is sufficient to collect enough information as to absorption/reflectivity of the gases along the sight path to distinguish 120 particular gases. The redirectable long path nature of the apparatus is such that a large area can be covered. The invention is applicable to a long path up to about 6 km in length (3 km out and back), enabling monitoring of over 36 times a larger area than other approaches. By taking wavelength specific measurements as a function of time, not only is the presence of a pollutant gas discernable, but a convenient automatic distance measurement by optical ranging determines the position of any reflecting target.

Figure 1:
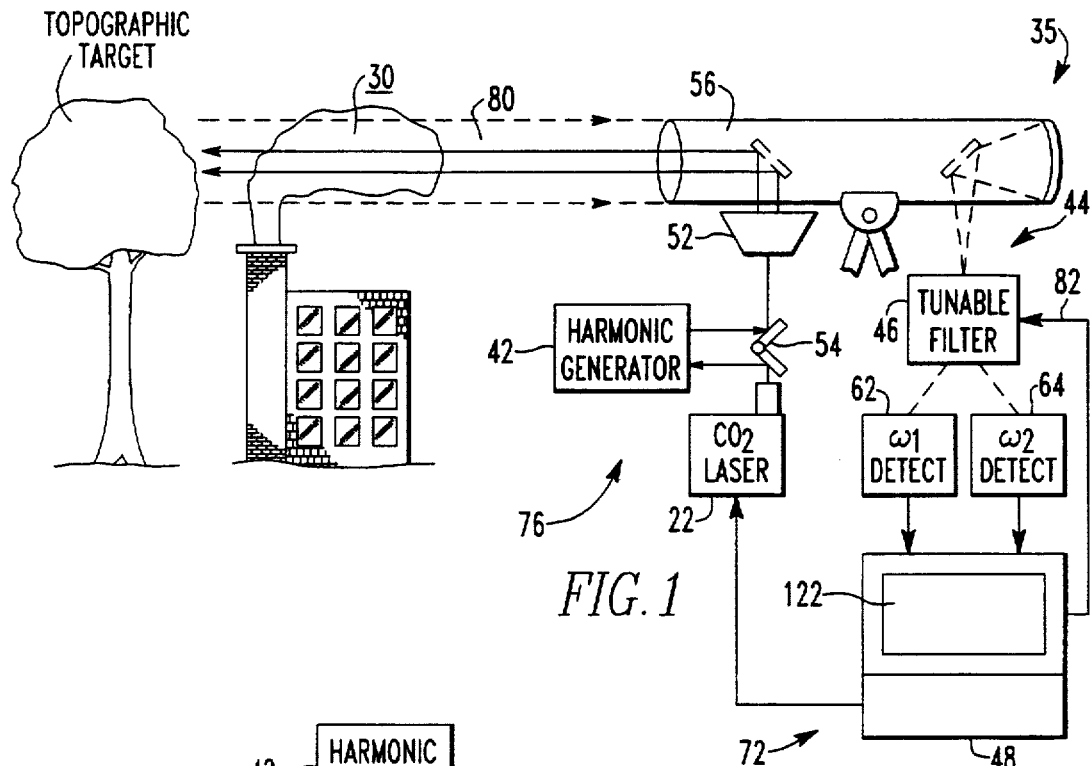
FIG. 1 is an overall block diagram showing a preferred embodiment of the apparatus according to the invention.
Figure 3:
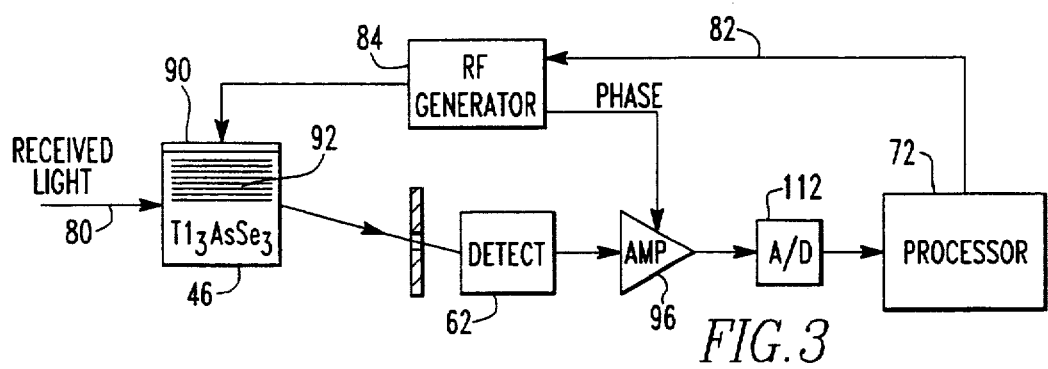
FIG. 3 is a schematic illustration showing application of the tunable optical filter.

FIG. 1 illustrates the elements of a preferred embodiment. The monitoring system 35 measures atmospheric absorption by hazardous air pollutants 30 over long paths, e.g., a 6 km path (3 km to a reflecting target), and the path is selectable manually by the operator or by automatic preprogrammed means. A 15 mJ pulsed $CO_2$ laser 22 is operated at a pulsed frequency of 300 Hz, at an optical wavelength from 9.2 to 10.8 μm. The intensities of light returning along the sight path from hazardous air pollutants, e.g., in a band from 9.2 to 10.8 μm, are measured and digitized, developing spectrographic information which is analyzed by the processor/controller 48, including a numerical processor 72 as shown in FIGS. 1 and 3, to assess the presence of selected gases.

An optional enhancement is preferably employed selectively to enlarge the optical illumination bandwidth. A harmonic generator or doubler 42 increases the $CO_2$ laser output frequencies into the 4.6 to 5.4 μm spectral range. The doubler 42 can be inserted automatically into the output illumination path for spectral analysis of absorption/reflectivity in this band.

As shown in FIG. 1, the hazardous air pollutants monitor 35 according to the invention comprises four main components. These are a $CO_2$ laser 22, a nonlinear crystal or doubler 42, a receiver 44 including an acousto-optic tunable filter 46, and a computer 48 for analyzing collected data and for controlling system operation. Preferably, these elements are coupled optically using a beam expander 52, a gimballed turning mirror 54, and a directable receiving telescope 56. The laser 22 and beam expander 52 direct illumination along the beam path 80, and are mounted commonly with the telescope 56 to illuminate and view along a common path between the measuring system 35 and a remote topographic target. The telescope 56 focuses light from the sample on at least one, and preferably two detectors 62, 64. The detectors, which may be point detectors, line arrays, or focal plane arrays, can include a 7-14 μm detector 62 and a 3.5-7 μm detector 64, which are operated selectively in conjunction with control of the illumination wavelength selected by the laser output means, generally designated 76. The detectors 62, 64 are controllably coupled to an electronic controller, preferably provided as a function of computer 48, that sequences system operation and analyzes the collected data to decode the measurement results.

The computer or other controller 48 cycles through a range of wavelengths, collecting spectrographic information regarding the absorption or reflection of light returning from the gas 30 and/or the topographic target. The computer then correlates the absorption lines detected in the spectrograph with particular gas compositions in the sample, and logs or reports the results.

The system as shown preferably also functions as a $CO_2$ laser range finder, determining the range of target gases by monitoring for the time difference between pulse generation and reception of the light reflected from the target gases. The thickness of the gas concentration 30 is likewise detected by monitoring for broadening of the pulse due to reflections of gases in the concentration 30 at different distances from the measurement system 35. The range finding function enables measurement of the distance to any reflecting target. Accordingly, no separate system is required for measuring distance, nor is it necessary to cross reference distance and absorption/reflectivity information in order to develop meaningful information.

The receiver portion 44 can be line-tuned for specific optical wavelengths, and the pulse/measurement operation can be accomplished at a high repetition rate (e.g., 300 Hz) for quick measurements sufficient to identify the absorption signatures of a number of different gases in the spectrographic data collected. The wavelength specific data is collected at the high resolution of the laser bandwidth ($\approx 0.01$ cm$^{-1}$).

The laser output means 76 and the telescopic input to the receiver 44 are mounted commonly. Accordingly, the measurement device 35 readily can be redirected at a new target, in real time, simply by redirecting the output beam. Thus, large areas can be quickly monitored by undertaking measurements along several beam paths. Similarly, the beam path can be changed quickly to respond to fugitive releases wherever they may occur or be suspected.

Figure 2:
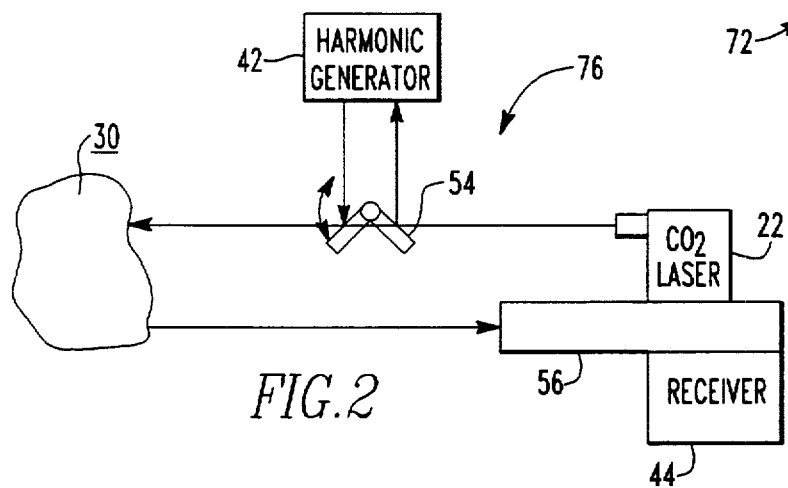
FIG. 2 is a schematic diagram showing the functional control and measurement arrangements of the components.

The $CO_2$ laser frequency preferably can be doubled via a nonlinear crystal 42 as shown in FIG. 2. The crystal can be a $Tl_3AsSe_3$ nonlinear crystal, as discussed in the infrared imaging patent disclosures discussed in the prior art section, above, which patents are hereby incorporated in their entireties. Preferably, the gimballed mirror 54 allows the laser beam to be directed through or around the doubler crystal 42, under control of the processor 48. Preferably, the apparatus 35 is controlled to analyze for absorption characteristics in a band centered at the basic laser wavelength, and then at the shorter harmonic wavelengths provided by the doubler crystal 42. An advantage of the shorter wavelengths provided by this option is that some gases (e.g., CO, NO, HBr, HI, OCS, and $N_2$) absorb in the 4.6 to 5.4 $\mu m$ range but not in the 9.2 to 10.8 $\mu m$ range. According to the invention, electronically activated two-position turning mirrors 54 direct the $CO_2$ laser beam through the crystal 42 for short wavelength operation and around the crystal 42 for long wavelength operation. The mirrors 54 can be operated by a control signal from the processor 48, which triggers operation of a solenoid or the like (not shown) to divert the mirrors 54 from the beam path or to insert the mirrors into the beam path and thereby redirect the beam through or around the doubler crystal 42 as required for that phase of system operation.

The telescope 56 collects and concentrates returning light on the acousto-optical filter 46. The filter 46 includes an acousto-optic $Tl_3AsSe_3$ material and an RF generator or oscillator 84, shown in FIG. 3. The oscillator 84 is controlled by the processor 48 for directing an acoustic wave through the crystal at a selected radio frequency, coupled to the crystal via transducer 90, bonded thereto. The acoustic wave fronts 92 form a diffraction grating in the crystal 46. By varying the acoustic frequency, the diffraction effects of the crystal 46 are changed, selectively varying the wavelength band applied to the detector 62 or 64, which can have a narrow slot input as shown in FIG. 3. The crystal of the tunable filter is used in this manner to direct a selected wavelength portion of the beam to the proper detector 62, 64. Two transducers 90 can be bonded to orthogonal faces of the crystal, for diffracting the incoming infrared radiation to the two detectors 62, 64.

The acousto-optical filter 46 has two key functions in the receiver 44. During absorption measurements, the narrow filter passband greatly increases the signal-to-noise ratio of the system by restricting the radiation applied to the detector 62, 64 from the atmosphere to a narrow spectral range, e.g., (2-10 cm$^{-1}$), around the absorption line which is then selected. The frequency of the acoustic beam determines the center wavelength of the optical passband and is electronically controlled to center the passband around the laser wavelength. During emission measurements, direct spectroscopy or derivative spectroscopy can be applied in which the acousto-optical filter 46 is tuned to between 3.5 and 14 $\mu m$. Sharp emission lines are measured by modulating the acoustic frequency at a fixed frequency, e.g., 1 KHz, to sinusoidally shift the passband of the acousto-optical filter. The modulation does not affect radiation which has a relatively constant intensity over the acousto-optical filter passband, but modulates the intensity from emission lines much narrower than the passband. A phase locked amplifier 96 tuned to the modulation frequency separates the modulated signal from the background. For narrow lines in a blackbody background at the same temperature, this approach gives a signal-to-background ratio of 11 at 10.6 $\mu m$, increasing to 43 at 5 $\mu m$.

The measurement system 35 can operate repetitively to sequence through a series of measurements intended to identify particular pollutant gases by their absorption spectra. Derivative spectroscopy can also be accomplished using the same equipment applied to the absorption measurements. In that case, the short laser pulse is replaced with a longer pulse to accommodate the slow modulation frequency. Key emission lines can be monitored during those scheduled times when absorption measurements are not being taken. If preset thresholds are exceeded in the absorption measurements (i.e., if the processor detects in the data a predetermined concentration of one or more pollutant gases), the system can be programmed to switch automatically to detailed measurements, selection of certain bands or wavelengths for more extensive analysis and/or selection of derivative spectroscopy measurements to supplement absorption measurements. This dual emission/absorption monitoring under automatic control of the processor/controller 48 reduces the volume of information that needs to be processed routinely, as compared to a system that collects all possible data all the time.

The processor 48 controls and sequences operations, and analyzes collected data for characteristic spectral lines. The processor 48 can comprise a commercial personal computer having data acquisition means 112 which sample and digitize the detector output levels, and one or more outputs 82 for controlling the tunable filter 46 and gimballed mirror arrangement 54. The processor 48 determines concentrations from the measured spectroscopic data. The processor 48 can include a numeric processor for analyzing the data and an electronic controller which may be a separate processor operable to control the laser, the acousto-optical tunable filter, and the directional optics. Alternatively, the numeric and control functions can be embodied in one computer 48.

Preferably, processed information from the data is displayed on a screen monitor 122. The raw and/or processed data can be stored on disc for later analysis, printed, reported remotely, used to trigger alarms, etc.

Whereas the measurement system as a whole can be oriented in any direction through the open air, the invention is able to probe regions inaccessible to point monitors. The measurement system 35 can be directed manually at desired target sites, or can be automatically positionable, e.g., by motor drives (not shown) under control of the processor 48. In this manner the processor 48 can sequence through measurements of a number of preprogrammed sites, and in each case measure and log information on the gases detected. The orientation of the measurement beam 80 can be encoded and stored with the spectral data, to associate the specific measurements with specific sites.

The processor 48 can proceed rapidly through a number of particular wavelength and illumination (absorption), excitation (fluorescence) and/or thermal emission measurement steps. Thus it is possible to determine concentrations of a large number of gases in minutes, rather than hours. The gases are sampled in-situ, thus avoiding losses of radicals that might occur from testing relying on sample collection and later testing.

Path-averaged measurements are available in this manner for accurate area monitoring. The system is further capable of responding rapidly to changing situations, e.g., the system can be arranged to hunt for fugitive releases or to take detailed measurements relating to a localized gas concentration such as the plume of a single stack.

There is a significant financial advantage to the automated monitor of the invention, particularly when large areas such as cities are to be monitored for a range of potential pollutants. Notably, the method and apparatus according to the invention is substantially less labor intensive than point monitoring, and at the same time provide advantages with respect to measurement capabilities over other monitoring techniques. Fluorescence, for example, has been used over long ranges at altitudes above 30,000 feet, but on the ground is primarily a point monitor.

A tunable diode forth of laser measurement according to the invention may become viable with the development of more powerful diode lasers become available, but is presently not preferred as being too restricted in power and wavelength coverage to be effective. Thus a controllably pulsed $CO_2$ laser is employed in the exemplary embodiment shown.

The differential absorption lidar approach is applicable to any pulsed laser range finding arrangement, and preferably is employed according to the invention as an analytical technique. Differential optical absorption spectroscopy normally encompasses the UV to near-IR regions, whereas Fourier transform infrared spectroscopy, like the present invention, is useful in the mid-to-far IR regions. Thus, a complete analysis system according to the invention employs differential optical absorption and the monitor discussed above, to encompass a full range of wavelengths of interest. It is also of course possible to restrict the function of the arrangement, for example, embodying the apparatus only to take path averaged absorption measurements or the like, for applications in which the full range of measurements are not needed.

Although the monitor of the invention does not cover the broad 3–13 $\mu$m absorption spectral range of Fourier transform infrared spectroscopy, the invention does cover the most important spectral ranges, i.e., those ranges in which most hazardous pollutants absorb. In any event, the monitor of the invention is substantially faster and less labor intensive than present techniques for measuring the concentrations of several gases.

In principle, a Fourier transform infrared spectrum can be collected in less then 10 ms. However, to achieve good sensitivity it is necessary to integrate the collected data over many measurements. A total time of about four minutes is thus used to integrate over 170 samples. By comparison the automated monitor according to the invention can integrate over 170 samples per gas in about 1 second, thus completing the analysis for 240 gases in the same four minutes.

In absorption measurements at short wavelengths, the invention has an operating distance and sensitivity comparable to a Fourier transform technique. However, the resolution of the monitor of the invention can be made narrower than with a Fourier transform technique. At the longer wavelengths containing the characteristic absorption lines of most hazardous pollutants, the $CO_2$ pulsed laser according to the invention is over 100 times brighter than the brightest incoherent sources, thereby making the invention much more sensitive than a Fourier transform analyzer and allowing the monitor to cover an area about 36 times larger than a Fourier transform infrared spectrometer. The monitor of the invention is 10 to 40 times more sensitive in emission measurements and encompasses the same wavelength range as a Fourier transform analyzer for this measurement application. The invention also enables measurement associated with fixed targets such as buildings or with mobile targets such as pollution clouds, whereas the known Fourier transform arrangement cannot. The invention thus has a major advantage in providing unattended automated operation and in localizing sources of fugitive releases.

The invention having been disclosed in connection with the foregoing variations and examples, additional variations will now be apparent to persons skilled in the art. The invention is not intended to be limited to the variations specifically mentioned, and accordingly reference should be made to the appended claims rather than the foregoing discussion of preferred examples, to assess the scope of the invention in which exclusive rights are claimed.

I claim:

1. An apparatus operable to remotely detect the presence of selected atmospheric gases in a sample, comprising:
    an infrared laser operable to emit a laser beam along a sight path intersecting the sample, the laser beam exciting gases in the sample at particular excitation wavelengths, thereby causing the gases to emit light at certain emission wavelengths, and to absorb light at certain absorption wavelengths, the emission wavelengths and the absorption wavelengths being characteristic of particular component gases in the sample;
    viewing means directed along the sight path for collecting light from the gases in the sample responsive to the laser beam;
    an acousto-optical tunable filter coupled to the viewing means, the tunable filter being operable controllably to diffract light collected by the viewing means for selecting particular optical wavelengths and to direct said particular optical wavelengths onto a detector means; and,
    an analyzer coupled to the detector means and to the tunable filter, the analyzer being operable to control the tunable filter for selecting a plurality of said particular optical wavelengths and to discriminate for presence of said particular component gases by determining a characteristic pattern of the emission and absorption wavelengths detected.

2. The apparatus according to claim 1, wherein said detector means comprises two detectors and further comprising memos for generating simultaneously two orthogonal acoustic waves in the acousto-optical filter at different frequencies, the two detectors receiving light from diffraction at the different frequencies, respectively, such that the two detectors measure two wavelengths simultaneously.

3. The apparatus according to claim 1, further comprising an output crystal between the laser and the sample, the output crystal producing a harmonic of a wavelength of the laser beam such that the gases are excited at a plurality of wavelengths.

4. The apparatus according to claim 3, further comprising means coupled to the analyzer, for switching the output crystal controllably into and out of the sight path.

5. The apparatus according to claim 4, wherein the means for switching the output crystal includes a gimballed mirror.

6. The apparatus according to claim 4, wherein the analyzer includes a processor operable to control the laser for providing a pulsed illumination along the sight path in an infrared band, the analyzer discriminating for both the absorption wavelengths and the emission wavelengths in the infrared band.

7. The apparatus according to claim 6, wherein said viewing means comprises a telescope, and wherein the laser and the telescope are mounted together on a movable mount defining the sight path, whereby the sight path can be redirected in open air.

8. The apparatus according to claim 6, further comprising a controllable oscillator controlled by the processor and coupled to the tunable filter for selecting said particular optical wavelengths directed onto the detector means, and wherein the processor is operable to discriminate for a plurality of emission and absorption spectral patterns characteristic of different gases.

9. The apparatus according to claim 8, wherein the acousto-optic tunable filter comprises $Tl_3AsSe_3$.

10. A method for remotely measuring atmospheric gases in a sample, comprising the steps of:
   directing an infrared laser beam through on the sample, so as to excite the sample and cause the sample to emit and to absorb light at particular wavelengths that are characteristic of component molecules in the sample;
   receiving the light from the sample and applying the light to an acousto-optical tunable filter having means for applying an acoustic wave at a predetermined frequency for diffracting the light into a spectrum, and applying the light to a detector;
   varying the predetermined frequency to select among a plurality of wavelengths of absorption and emission at the particular wavelengths that are characteristic of the component molecules;
   measuring a level of the light at said particular wavelengths;
   analyzing a pattern of the light, at the particular wavelengths for detecting the component molecules in the sample.

11. The method according to claim 10, further comprising redirecting the infrared laser beam for selecting the sample by selecting a sight path.

12. The method according to claim 11, further comprising generating harmonics in the laser beam so as to excite the sample at a plurality of wavelengths.

13. The method according to claim 12, comprising repetitively pulsing the laser and analyzing successively for particular wavelengths characteristically absorbed by at least one pollutant gas.

14. A method for remotely measuring atmospheric gases in a sample, comprising the steps of:
   providing an exciting light beam via an infrared laser controllably operable to emit at selected wavelengths, and mounting the laser to emit along a beam path intersecting the sample such that the laser excites component molecules in the sample;
   receiving infrared radiation from the sample, the infrared radiation having absorption and emission spectra characteristic of the component molecules;
   applying the infrared radiation to an acousto-optical tunable filter and an associated detector means, and tuning the filter by applying to the filter an acoustic wave at an predetermined frequency to diffract the infrared radiation such that a selected wavelength is applied to the detector means;
   measuring a level of said infrared radiation at the selected wavelength;
   tuning the filter by successively applying additional frequencies, measuring the level at the additional selected wavelengths, and proceeding through a set of frequencies sufficient to define the absorption and emission spectra of the sample; and,
   determining the component molecules of the sample from the absorption and emission spectra.

15. The method according to claim 14, further comprising redirecting the laser beam to select the sample.

16. The method according to claim 14, further comprising inserting an output crystal into the beam path and directing the laser beam through the output crystal for obtaining a plurality of simultaneous wavelengths of illumination.

17. The method according to claim 14, further comprising varying an output wavelength of the infrared laser so as to select an illumination wavelength, tuning the filter and defining the absorption and emission spectra under illumination at a plurality illumination wavelengths.

18. The method according to claim 17, wherein said detector means comprises two detectors and the method further comprises applying to the filter a second, orthogonal acoustic wave; simultaneously diffracting the infrared radiation along separate paths to the two detector; and measuring the level at two different selected wavelengths simultaneously.

19. An apparatus operable to remotely detect the presence of selected atmospheric gases in a sample,
   an infrared laser controllably operable to emit a laser beam along a sight path intersecting the sample, the laser beam having an on-state and an off-state, the laser exciting gases in the sample at particular excitation wavelengths when in the on-state, thereby causing the gases to emit light at certain emission wavelengths, and to absorb light at certain absorption wavelengths, the emission wavelengths and the absorption wavelengths being characteristic of particular component gases in the sample;
   viewing means directed along the sight path for collecting light from the gases in the sample responsive to the laser beam;
   an acousto-optical tunable filter coupled to the viewing means, the tunable filter being operable controllably to diffract light collected by the viewing means for selecting particular optical wavelengths and to direct said particular optical wavelengths onto a detector;
   an analyzer coupled to the detector and to the tunable filter, the analyzer being operable to control the tunable filter for selecting a plurality of said particular optical wavelengths and to discriminate for presence of said particular component gases by determining a characteristic pattern of the emission and absorption wavelengths detected; and,
   wherein the analyzer is operable to collect the emission wavelengths during the off-state of the laser.

* * * * *